(12) United States Patent
Abraham et al.

(10) Patent No.: US 10,092,373 B2
(45) Date of Patent: Oct. 9, 2018

(54) ORTHODONTIC TREATMENT PLANNING USING LIP TRACER

(71) Applicant: OraMetrix, Inc., Richardson, TX (US)

(72) Inventors: Charles L Abraham, Richardson, TX (US); Phillip Getto, Plano, TX (US); Peer Sporbert, Berlin (DE); Markus Kaufmann, Berlin (DE)

(73) Assignee: OraMetrix, Inc., Richardson, TX (US)

( * ) Notice: Subject to any disclaimer, the term of this patent is extended or adjusted under 35 U.S.C. 154(b) by 0 days.

(21) Appl. No.: 14/145,996

(22) Filed: Jan. 1, 2014

(65) Prior Publication Data

US 2015/0182303 A1  Jul. 2, 2015

Related U.S. Application Data

(60) Provisional application No. 61/748,076, filed on Jan. 1, 2013.

(51) Int. Cl.
*A61C 7/00* (2006.01)
*A61C 9/00* (2006.01)

(52) U.S. Cl.
CPC ............ *A61C 7/002* (2013.01); *A61C 9/0053* (2013.01)

(58) Field of Classification Search
CPC .......... A61C 7/002; G06T 2207/30036; G06F 19/3437
USPC .......................................................... 433/24
See application file for complete search history.

(56) References Cited

U.S. PATENT DOCUMENTS

| | | | | |
|---|---|---|---|---|
| 6,845,175 | B2* | 1/2005 | Kopelman et al. | 382/154 |
| 7,156,655 | B2* | 1/2007 | Sachdeva et al. | 433/24 |
| 7,234,937 | B2* | 6/2007 | Sachdeva et al. | 433/24 |
| 7,292,716 | B2* | 11/2007 | Kim | 382/128 |
| 8,092,215 | B2* | 1/2012 | Stone-Collonge et al. | 433/24 |
| 8,386,061 | B2* | 2/2013 | Violante et al. | 700/98 |
| 8,423,335 | B2* | 4/2013 | Methot | 703/6 |
| 8,650,005 | B2* | 2/2014 | Liao | 703/1 |
| 8,706,672 | B2* | 4/2014 | Malfliet et al. | 706/47 |
| 9,421,074 | B2 | 8/2016 | Sachdeva et al. | |
| 2013/0218530 | A1* | 8/2013 | Deichmann et al. | 703/1 |
| 2014/0122027 | A1* | 5/2014 | Andreiko et al. | 703/1 |

(Continued)

OTHER PUBLICATIONS

David M. Sarver, DDM, MS, American Journal of Orthodontics and Dentofacial Orthopedics, vol. 120, No. 2, The importance of incisor positioning in the esthetic smile: The smile arc (2001).

(Continued)

*Primary Examiner* — Ralph Lewis
(74) *Attorney, Agent, or Firm* — McDonnell Boehnen Hulbert & Berghoff LLP

(57) ABSTRACT

The present invention discloses orthodontic treatment planning which enables designing the desired smile line with the help of a computer workstation.
A new lip trace feature enables cutting out the portion of a photograph corresponding to the area inside the lips. The 3D model of the teeth is then completely visible when overlaid with the facial photograph.
One can use this feature to superimpose the patient photo over the 3-D model of the teeth to see how much intrusion or extrusion is needed to design the smile line.
Three dimensional model of dentition obtained by scanning of teeth along with the patient's two dimensional facial photograph is used to design the desired smile line for the patient by means of software instructions in the workstation.

9 Claims, 2 Drawing Sheets

(56) References Cited

U.S. PATENT DOCUMENTS

2014/0329194 A1    11/2014   Sachdeva et al.
2014/0342304 A1*  11/2014   Meletiou, Jr. .................. 433/29

OTHER PUBLICATIONS

Nayda Rondon, Anatomy of a Smile, available at http://www.yourdentistryguide.com/smile-anatomy/ (copyright 2006-2017).

* cited by examiner

ORTHODONTIC TREATMENT PLANNING USING LIP TRACER

CROSS-REFERENCE TO RELATED APPLICATIONS

This application is a non-provisional application of the provisional application, Ser. No. 61/748,076, filed Jan. 1, 2013. Priority of the filing date of the provisional application is hereby claimed for the instant application. The subject matter of this application is related to the subject matter of the following applications. Priority to the related applications is not claimed under 35 U.S.C. §120.

Application Ser. No. 13/107,913, filed May 15, 2011, pending; provisional application Ser. No. 61/642,646, filed May 4, 2012; and non-provisional application Ser. No. 13/887,323, pending.

The entire contents of each of the above listed patent applications are incorporated by reference herein.

BACKGROUND OF THE INVENTION

A. Field of the Invention

This invention relates generally to the field of orthodontics. More particularly, the invention relates to planning orthodontic treatment for a patient using lip tracer.

B. Description of Related Art

There are numerous patents issued in the area of orthodontic treatment planning to cure mal-occlusion of a patient. However, they lack in the area of planning the treatment in order to provide proper smile.

The present invention meets this need.

SUMMARY OF THE INVENTION

The present invention discloses orthodontic treatment planning which enables designing the desired smile line with the help of a computer workstation.

A lip trace feature is disclosed which enables the user in cutting out the portion of a facial photograph corresponding to the area inside the lips. The 3D model of the teeth is then completely visible when overlaid with the facial photograph.

One can use this feature to see how much intrusion or extrusion is needed to design the smile line during the treatment planning.

Three dimensional model of dentition obtained by scanning of the patient's teeth along with the patient's two dimensional facial photograph is used to design the desired smile line for the patient by means of software instructions in the workstation.

BRIEF DESCRIPTION OF THE DRAWINGS

Presently preferred embodiments of the invention are described below in reference to the appended drawings, wherein like reference numerals refer to like elements in the various views, and in which.

DETAILED DESCRIPTION OF PREFERRED EMBODIMENT

A lip trace feature is disclosed which enables cutting out the portion of a digital facial photograph corresponding to the area inside the lips using a computer workstation. The 3D model of the patient's teeth is then completely visible when overlaid with the modified facial photograph.

This feature is used to see how much intrusion or extrusion is needed in order to design the smile line during the orthodontic treatment of a patient.

The process is described below.

Figure 1:
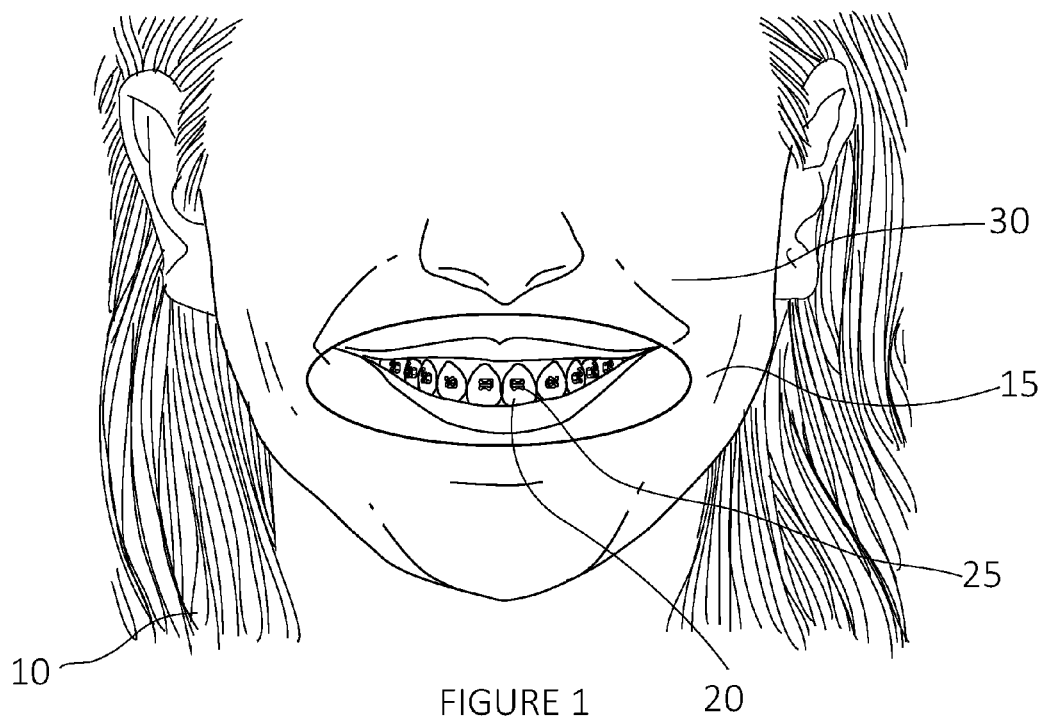
FIG. 1 shows the virtual 2-D photograph of the patient's face.

Step 1. A digital facial photograph of a patient is selected by an user from a collection in the workstation and placed in the first window on the screen display of the workstation. A digital copy of the same facial photograph is then placed in the second window on the display of the workstation. Preferably, the facial photograph selected shows a smiley face. For example, FIG. 1 shows a digital copy of the facial photograph 10 of the patient in the second window on the display of the workstation.

Step 2. Lip Trace function is then invoked in the second window by the user in conjunction with the digital copy of the facial photograph. The workstation software provides this capability. The user then identifies the general area from which the desired cut-out on the facial photograph in the second window will be performed; e.g., the area 15 in FIG. 1. The user then invokes the 'Add Lip Trace' function from the Lip Trace function and, with the help of the curser attached to the workstation, marks the actual area inside the lips, including teeth, to be cut-out from the facial photograph in the second window; for example the patient's teeth 20, including the brackets 25 attached to teeth 20, and the surrounding areas inside the lips as shown in FIG. 1. Marking the actual area inside the lips defines the 'smile line.' The workstation software automatically and simultaneously transfers the tasks performed on the facial photograph in the second window, e.g. marking the area 15 and marking of the actual area inside the lips, including teeth and brackets to be cut-out, to the facial photograph in the first window.

Figure 2:
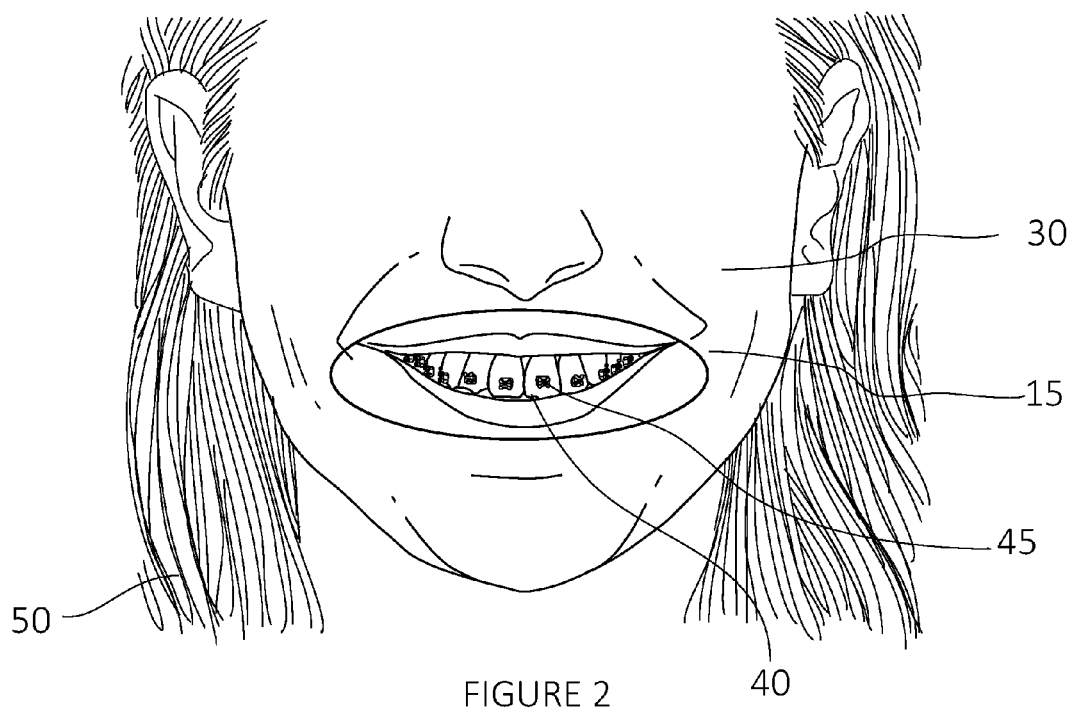
FIG. 2 show a copy of the photograph of FIG. 1 superimposed after cutting out the portion of the facial photograph corresponding to the area inside the lip on the virtual three-dimensional model of the teeth of the patient.

Step 3. A virtual three dimensional model of the patient's teeth is placed in the first window behind the facial photograph. This can be done prior to Step 1, during Step 1 or at the beginning of Step 3. After Step 2 is completed, the user clicks on the 'Synchronize Image Fade' icon on the workstation display; which causes proper synchronization of the placement of the patient's teeth in the virtual three dimensional model with the facial photograph of the patient in the first window, and simultaneous cut-out of the actual area inside the lips marked for removal in Step 2 from both the facial photographs in the first and second windows; thereby making the teeth from the virtual three dimensional model of the patient visible along with the modified facial photograph in the first window. When the brackets are placed on the patient's teeth, their placement on the facial photograph can be used in conjunction with the brackets placed on the teeth in the virtual three dimensional model for achieving synchronization. Otherwise, some other markers placed both in the facial photograph and in the virtual three dimensional model can be used for synchronization. The result is displayed in FIG. 2. FIG. 2 shows the modified facial photograph 50 of the patient in the first window, including the teeth 40 from the virtual three dimensional model along with the portion 30 of the face from FIG. 1 that remained after the cut-out of the area inside the lips, including teeth 20 and brackets 25. In this case, the virtual three dimensional model of the patient's teeth includes the brackets 45 attached to the teeth. General marked area 15 in FIG. 1 for the lip trace cut-out also is marked automatically in FIG. 2.

Step 4. See how much intrusion or extrusion is needed in order to design the smile line during planning or review of the orthodontic treatment of the patient. The virtual treatment simulation can be performed on the workstation in order to find acceptable solutions to correct the problems.

The Lip Trace function provides additional functionality as well, such as:
  a. "Subtract Lip Trace' function provides the capability to erase a portion of the lip trace added with the 'Add Lip Trace' function in order to make corrections.
  b. Prior lip trace can be saved; and retrieved in future using 'Show Lip Trace' function.
  c. 'Delete Lip Trace' enables removal of the lip trace.

The virtual three dimensional model of the teeth of a patient can be obtained by in-vivo scanning of the dentition of the patient. This virtual dentition model can be obtained for teeth without bonded brackets or with bonded brackets. A white-light scanner can be used to obtain virtual images of the dentition from which the virtual three dimensional model can be derived.

The workstation also provides 'Show/Hide Gingiva' menu option to turn on/off the model's gingiva, when included in the three dimensional virtual model of the teeth of the patient, obtained through in-vivo scanning, for a more lifelike appearance.

Synchronize Image Fade button can be used to toggle the lip cutout on or off as desired during simulation of the treatment planning or review.

In summary, the present invention discloses orthodontic treatment planning which enables designing the desired smile line with the help of a computer workstation.

A new lip trace feature enables cutting out the portion of a photograph corresponding to the area inside the lips. The 3D model is then completely visible when overlaid with the facial photograph.

One can use this feature to superimpose the patient photo over the 3-D model of the teeth to see how much intrusion or extrusion is needed to design the smile line.

Three dimensional model of dentition obtained by scanning of teeth along with the patient's two dimensional facial photograph is used to design the desired smile line for the patient by means of software instructions in the workstation.

Presently preferred and alternative embodiments of the invention have been set forth. Variation from the preferred and alternative embodiments may be made without departure from the scope and spirit of this invention.

We claim:

1. A method of designing smile line for orthodontic treatment of a patient using a computer workstation, comprising the steps of:
  a. placing a digital facial photograph of said patient in a first window on screen display of said workstation; and a digital copy of said facial photograph in a second window on display of said workstation;
  b. marking area inside lips to be cut-out from said facial photograph in said second window;
  c. placing a virtual three dimensional model of said patient's teeth in said first window behind said facial photograph in a manner such that said virtual three dimensional model is synchronized with said facial photograph;
  d. synchronizing placement of said patient's teeth in said virtual three dimensional model with said facial photograph of said patient in said first window;
  e. performing cut-out of said area inside said lips marked in step b. for removal from said facial photograph in said second window;
  f. simultaneously performing cut-out of same area inside lips from said facial photograph in said first window; thereby making said teeth from said virtual three dimensional model of said patient visible along with said facial photograph in said first window modified with said cut-out;
  g. examining said teeth from said virtual three dimensional model of said patient in conjunction with said facial photograph in said first window; and
  h. determining an amount of intrusion or extrusion required to align the edges of the upper teeth against the lower lip by superimposing the facial photograph over the three dimensional model of the teeth.

2. The method of claim 1, wherein said patient is smiling in said digital facial photograph.

3. The method of claim 1, wherein said virtual three dimensional model of said patient's teeth include brackets bonded to said teeth.

4. The method of claim 1, wherein in steps g and h virtual treatment simulation can be performed on the workstation in order to find acceptable solutions to correct problems.

5. The method of claim 1, wherein said area marked inside lips to be cut-out can be modified.

6. The method of claim 1, wherein said virtual three dimensional model of said teeth of a patient is obtained by in-vivo scanning of dentition of said patient.

7. The method of claim 1, wherein a white-light scanner is used to obtain virtual images of dentition from which said virtual three dimensional model is derived.

8. The method of claim 1, wherein said workstation provides 'Show/Hide Gingiva' menu option to turn on/off said virtual three dimensional model's gingiva, when included in the three dimensional virtual model of the teeth of the patient, obtained through in-vivo scanning, for a more lifelike appearance.

9. The method of claim 1, wherein Synchronize Image Fade button can be used to toggle said lip cutout on or off as desired during simulation of treatment planning or review.

* * * * *